United States Patent [19]

Gross et al.

[11] Patent Number: 5,262,315
[45] Date of Patent: Nov. 16, 1993

[54] PRODUCTION OF VANILLIN BY BIOCONVERSION OF BENZENOID PRECURSORS BY PYENOPORUS

[75] Inventors: Brigitte Gross, Viroflay; Marcel Asther, Maurepas; Georges Corrieu, Viroflay; Pascal Brunerie, Saint-Maur, all of France

[73] Assignee: Pernod Ricard, Paris, France

[21] Appl. No.: 879,449

[22] Filed: May 1, 1992

Related U.S. Application Data

[63] Continuation of Ser. No. 686,940, Apr. 18, 1991, abandoned.

[30] Foreign Application Priority Data

Apr. 19, 1990 [FR] France .................... 90 05003

[51] Int. Cl.$^5$ .................................... C12P 7/24
[52] U.S. Cl. .................... 435/147; 435/171; 435/254.1
[58] Field of Search ............ 435/156, 147, 121, 254

[56] References Cited

U.S. PATENT DOCUMENTS

| | | | |
|---|---|---|---|
| 4,686,183 | 8/1987 | Abraham et al. | 435/158 |
| 4,755,466 | 7/1988 | Yokozeki et al. | 435/108 |
| 4,968,608 | 11/1990 | Giacobbe et al. | 435/71 |
| 5,017,479 | 5/1991 | Eyssautier | 435/101 |

FOREIGN PATENT DOCUMENTS

667673A5 10/1988 Switzerland.

OTHER PUBLICATIONS

Dart et al., "The Metabolism of Coniferyl Alcohol by *Polyporus dichrous*", *Chemical Abstracts*, 98:50120h, 1983.

Haraguchi et al., "Degradation of Lignin by Wood--Rotting Fungi . . . *Pycnoporus coccineus*", *Chemical Abstracts*, 70:30227s, 1969.

Gallette, et al., "HPLC Characterization of Phenolics in Lignocellulosic Materials", *Chemical Abstracts*, 110:227932u, 1989.

Nazareth et al., "Degradation of Funlic Acid via 4-Vinylguaiacol by *Fusarium solani* (Mart.) sacc," *Can. J. Microbiol.*, vol. 32, pp. 494-497, 1986.

Raroute et al., "Metabolism of Ferulic Acid by *Paicilomyces variotii*—and *Pestalotin palmarum*", *Appl. and Environ Monobiology*, vol. 55, No. 9, pp. 2391-2398, 1989.

Agosin, E. et al., J. Sci. Food Agric. 36: 925-935 (1985).
Tadasa, K., Agric. Biol. Chem. 41(6): 925-929 (1977).
Dart, R. K. et al., Microbios. Letters, 20: 81-94 (1982).
Haraguchi, T., Mokuzai Gakkaishi 14: 214-219 (1968).
Galletti, G. C. et al., Chromatographia 26: 191-196 (1988).

*Primary Examiner*—Marian C. Knode
*Attorney, Agent, or Firm*—Finnegan, Henderson, Farabow, Garrett & Dunner

[57] ABSTRACT

The present invention relates to a process for producing vanillin. Culturing of a basidiomycete fungus of the genus Pycnoporus or of their variants and mutants is performed in a culture medium to which a benzenoid precursor of vanillin has been added, and the vanillin produced by bioconversion of the benzenoid precursor is recovered.

10 Claims, 5 Drawing Sheets

FIG_1

FIG_2

PRODUCTION OF VANILLIN BY BIOCONVERSION OF BENZENOID PRECURSORS BY PYENOPORUS

This application is a continuation of application Ser. No. 07/686,940, filed Apr. 18, 1991, now abandoned.

FIELD OF THE INVENTION

The present invention relates to a process for producing vanillin by bioconversion of benzenoid precursors.

SUMMARY OF THE INVENTION

Vanillin is currently obtained either by chemical synthesis, or in the natural state by extraction from vanilla pods.

The object of the present invention is to obtain a process for producing vanillin which is simple to industrialize and which makes it possible to obtain a vanillin which may be considered under the regulations in force, in particular in the EEC countries, to be natural. Such is the case with the products obtained by bioconversion of natural precursors by means of microorganisms.

PREFERRED EMBODIMENTS OF THE INVENTION

To this end, the subject of the present invention is a process for producing vanillin, wherein culturing of a basidiomycete fungus of the genus Pycnoporus or of their variants and mutants is performed in a culture medium to which a benzenoid precursor of vanillin has been added, and wherein the vanillin produced is recovered after bioconversion of said precursor, the Pycnoporus strain being selected for its metabolic property of degrading said precursors with accumulation of vanillin in the medium.

As a benzenoid precursor, derivatives at the 1-position of 4-hydroxy-3-methoxybenzene, such as vanillic acid or ferulic acid, will be used in particular.

In an especially suitable implementation, the fungus of the species *Pycnoporus cinnabarinus* will be used, in particular the strains CNCM Nos. I-937 and I-938 or their variants and mutants which possess the metabolic property of producing a high level of degradation of benzenoid precursors of vanillin such as ferulic acid, with accumulation of vanillin in the medium.

Advantageously, precursors originating from natural plant substrates, preferably rich in said precursors, will be used. There may be mentioned ferulic acid, which is present in the cell membranes of many monocotyledons and dicotyledons such as, for example, sugar-beet pulp, a byproduct of the sugar industry, or aleurone grains of wheat or of different cereals. The natural sources of ferulic acids are hence relatively abundant. Another benzenoid precursor of natural origin which is useable according to the invention is isoeugenol.

Moreover, compounds such as para-hydroxybenzoic acid, para-hydroxybenzaldehyde, vanillyl alcohol and stilbenes, inter alia, may be used.

In a preferred embodiment of the process according to the invention, the fungus is first cultured in an agitated liquid medium, and the precursor is added only after a large biomass, possessing optimal enzymatic capacity for bioconversion of said precursor, is obtained.

Thus, advantageously, in the case of culture of the fungus *Pycnoporus cinnabarinus*, the precursor is added when the necessary biomass is obtained, namely 3 days under the culture conditions of the medium of Appendix 2, described in detail below.

When the precursor is added at the start of culturing, bioconversion to vanillin is observed but with much lower yields.

In a particular embodiment of the process according to the invention, the inoculum via which the fungus is inoculated into the culture medium consists of mycelium fragments or spores, or precultures of these inocula.

A quantity of precursors ranging up to 50 g/ml per culture medium may be introduced.

In the process according to the invention, at least 15 mycelium fragments per 100 ml of culture medium and $10^5$ to $10^7$ spores/ml of medium will be used. The pH of the culture medium can be between 2.5 and 6.5. The incubation temperature of the cultures can be between 25° and 40° C.

Advantageously, the vanillin is recovered when the precursor is no longer detectable in the culture medium and before its bioconversion to vanillyl alcohol.

To recover the vanillin, it is possible, according to processes known to those skilled in the art, to extract it from the culture media with solvents, followed by a distillation; it is also possible to perform a fractional crystallization or a preparative industrial chromatography directly on the culture media.

According to the process according to the invention, the precursor may be introduced sequentially or in continuous fashion, and the vanillin may likewise be recovered sequentially or in continuous fashion.

Under the culture conditions of the medium of Appendix 2 described in detail below, the vanillin is recovered 4 or 5 days after the introduction of the precursor.

Other features and advantages of the present invention will become apparent in the light of the detailed description which follows.

In the description, reference is made to FIGS. 1 to 5.

EXAMPLES

I - Bioconversion Protocol

1) Principle

Figure 1:
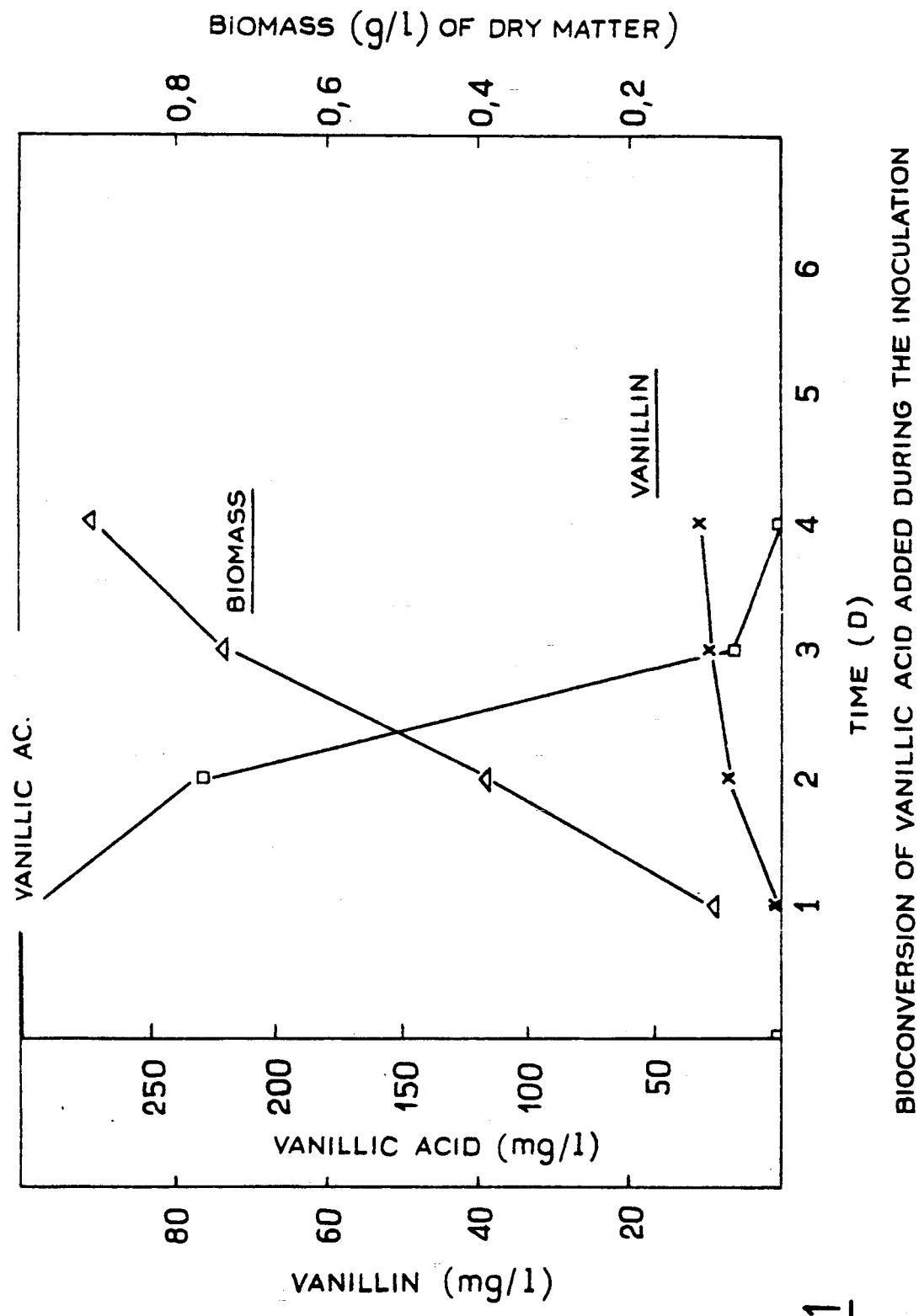
FIG. 1 shows the bioconversion of vanillic acid added during the inoculation.

The filamentous basidiomycete fungus is cultured beforehand in an agitated liquid medium in order to obtain a large biomass possessing the enzymatic capacity needed for bioconversion, as well as a sufficient yield. After a few days of culture, the sterile precursor is added aseptically. Disappearance of the precursor (ferulic acid or vanillic acid) and bioconversion to vanillyl alcohol and vanillic acid (in the case of ferulic acid) are monitored by HPLC analysis.

2) Strains Used

Two basidiomycetes of the species *Pycnoporus cinnabarinus* deposited at the Collection Nationale de Culture de Microorganisme (National Collection of Microorganism Cultures) of the Pasteur Institute (CNCM) under Nos. I-937 and I-938 on Apr. 10, 1990.

3) Inoculum Production

Three types of inoculum are possible: they are, respectively, spores or mycelium fragments or a preculture of these.

a) Production of Spores 250 ml of sporulation medium (composition given in Appendix 1) are inoculated in a Roux flask with mycelium fragments from culture on an agar medium. Incubation is carried out at 37° C. for three weeks. During this period, the mycelium develops on the agar surface, producing conidia (spores). These spores are detached from the surface of the solid culture by the agitation of glass beads immersed in sterile aqueous physiological solution. The spore suspension thereby obtained is filtered through glass wool in order to remove all large mycelial fragments. Counting is carried out on a Thoma cell. The inoculum of the cultures may then be quantified using an aliquot of known volume of this solution.

| Appendix 1: Composition of the solid sporulation medium | |
|---|---|
| Yeast extract | 3 g/l |
| Malt extract | 3 g/l |
| Bacto peptone | 5 g/l |
| Glucose | 10 g/l |
| Agar | 15 g/l |
| Biotin, 0.5 ml/l of a 0.001% sterile solution | |
| Solution of salts (1) | 20 ml/l |
| (1) Solution of salts | |
| $Na_3$ citrate.$2H_2O$ | 125 g/l |
| $KH_2PO_4$ (anhydrous) | 250 g/l |
| $NH_4NO_3$ (anhydrous) | 100 g/l |
| $MgSO_4.7H_2O$ | 10 g/l |
| Solution of trace elements (2) | 5 ml/l |
| (2) Solution of trace elements | |
| Citric ac.$H_2O$ | 50 g/l |
| Zinc sulfate | 50 g/l |
| Copper sulfate | 2.5 g/l |
| Manganese sulfate | 0.5 g/l |
| Boric ac. | 0.5 g/l |
| $Na_2MoO_4.2H_2O$ | 0.5 g/l |
| $Fe(NH_4)_2(SO_4)_2.6H_2O$ | 10 g/l | b) Production of Mycelium Fragments

A solid medium (20 g/l of malt extract +15 g/l of agar +2 g/l of yeast extract) in a Petri dish is inoculated centrally with a mycelium fragment from culture on agar medium. Incubation is carried out at 37° C. until the mycelium completely covers the surface. Fragments of this mycelium are then used as an inoculum; the mycelium fragments are cut out with a hollow punch approximately 4 mm in diameter.

c) Production of a Mycelium Preculture

An incubation of the spores or mycelium fragments is carried out in a volume of medium (5 to 10% of the final volume of the culture) and then used as an inoculum.

4) Carrying Out the Culturing 100 ml of medium conventionally containing, in particular, an animal or vegetable carbon source, inorganic salts and vitamins (a detailed composition of the culture medium used is given in Appendix 2) are used in an Erlenmeyer of capacity 500 ml. Inoculation is performed either with mycelium fragments (15 to 30 per culture) or with spores on the basis of $2 \times 10^5$ spores/ml of medium. The cultures are incubated at 37° C. and subjected to a rotary agitation at 120 rpm with an amplitude of 6 cm.

| Appendix 2: Composition of the culture medium | |
|---|---|
| Maltose | 20 g/l |
| Diammonium tartrate | 1.8415 g/l |
| $KH_2PO_4$ | 0.2 g/l |
| $CaCl_2.2H_2O$ | 0.0132 g/l |
| $MgSO_4.7H_2O$ | 0.5 g/l |
| Yeast extract | 0.5 g/l |
| Thiamine hydrochloride | 2.5 mg/l |
| Sterilization by autoclaving: | 120° C. - 20 min. |

5) Supplementation of the Cultures With Precursor

After 72 h of culture, sterile ferulic acid or sterile vanillic acid is added in the proportion of 0.3 g/l of culture. The ferulic acid and vanillic acid are used:
either in the form of crystals, autoclaved,
or in the form of a salt in water (for example the $Na^+$, $K^+$ or $NH_4^*$ salt) and sterilized by filtration (porosity: 0.2 μm).

6) Monitoring of the Rate of Conversion of a Culture a) Sampling

Every day, once the culture has been supplemented with precursor, 1.5 ml of each culture is withdrawn under sterile conditions. This aliquot is filtered through a hydroprobic membrane (porosity:0.2 μm) pretreated with methanol and an HPLC analysis of the filtrate is carried out.

b) HPLC Analysis reversed phase:bondapack C18 column
solvent:0.01% $CH_3COOH$ in $H_2O$/methanol
UV detection at 280 nm
injected sample volume:10 to 150 μl Retention Time of the Compounds Analyzed vanillyl alcohol:10 min
vanillic acid:14 min
vanillin:16 min
ferulic acid:18 min

7) Measurement of the Biomass ("False Reaction Rate")

This measurement necessitates "sacrifice" of the culture; the results obtained under these conditions do not correspond to a true picture of the reaction rate, since the same culture is not monitored throughout the study.

The 100 ml cultures are filtered through a previously tared glass fiber membrane. The biomass collected is placed for 24 h at 100° C. The corresponding dry matter content is determined by weighing.

II - Results

Example using the strain No. I-937 (the same results were obtained with the strain No. I-938.)

1) Bioconversion of Vanillic Acid a) Results With Measurement of the Biomass ("False Reaction Rate")

| PRECURSOR ADDED DURING THE INOCULATION (see FIG. 1) | | | |
|---|---|---|---|
| Age of the culture (in d) | Biomass (in g of dry matter per liter) | Vanillic acid precursor (in mg/l) | Vanillin (in mg/l) |
| 0 | | 310 | |
| 1 | 0.088 | 314 | |
| 2 | 0.389 | 228 | 6.8 |
| 3 | 0.737 | 18 | 9.2 |
| 4 | 0.911 | 0.3 | 10.7 |

A rapid and total consumption of vanillic acid is observed in 3–4 days of culture. The microbial biomass increases up to the last day of analysis. Vanillin synthesis is detected from day two onwards, and the quantity of vanillin accumulated is rising up to the last day of the study. The maximum molar yield of conversion to vanillin is low: 3.8%.

Figure 2:
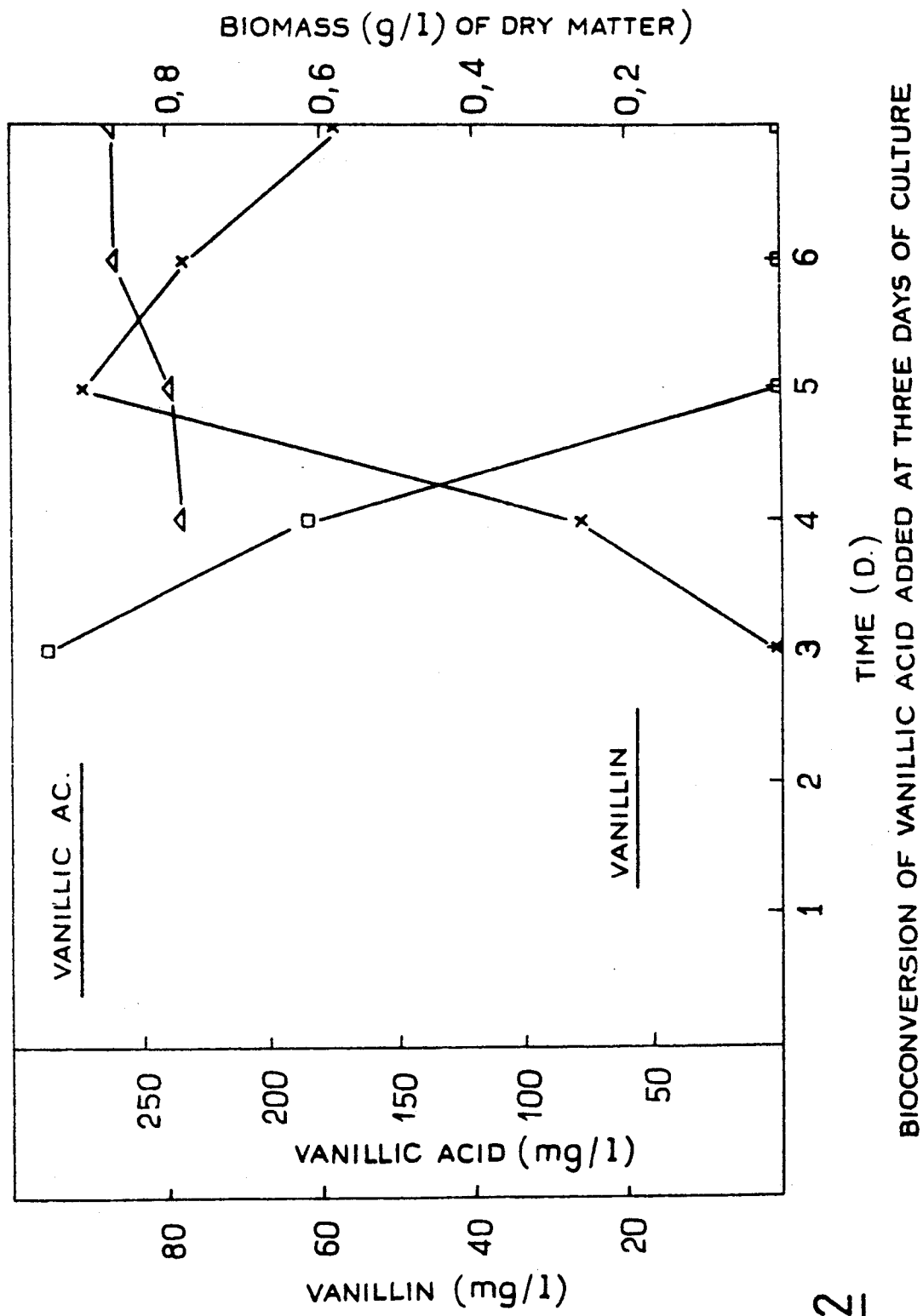
FIG. 2 shows the bioconversion of vanillic acid added at 3 days of culture.

| PRECURSOR ADDED ON DAY THREE OF CULTURE (see FIG. 2) | | | |
|---|---|---|---|
| Age of the culture (in d) | Biomass (in g of dry matter per liter) | Vanillic acid precursor (in mg/l) | Vanillin (in mg/l) |
| 3 | | 286 | |
| 4 | 0.782 | 184.5 | 25.6 |
| 5 | 0.798 | 0 | 90.8 |
| 6 | 0.869 | 0 | 78 |
| 7 | 0.872 | 0 | 58 |

The consumption of vanillic acid is more rapid than in the above case: in 2 days, the precursor concentration has fallen to 0 mg/l. The microbial biomass increases little after the time of introduction of vanillic acid. Vanillin synthesis is virtually immediate, and a maximum content is attained 2 days after the supplementation. Beyond this point, vanillin disappears very rapidly from the medium. In this case, the maximum molar yield of conversion to vanillin is much higher than before: 35.1%.

b) Results Reflecting the True Reaction Rate, With Assay of Vanillyl Alcohol

Figure 3:
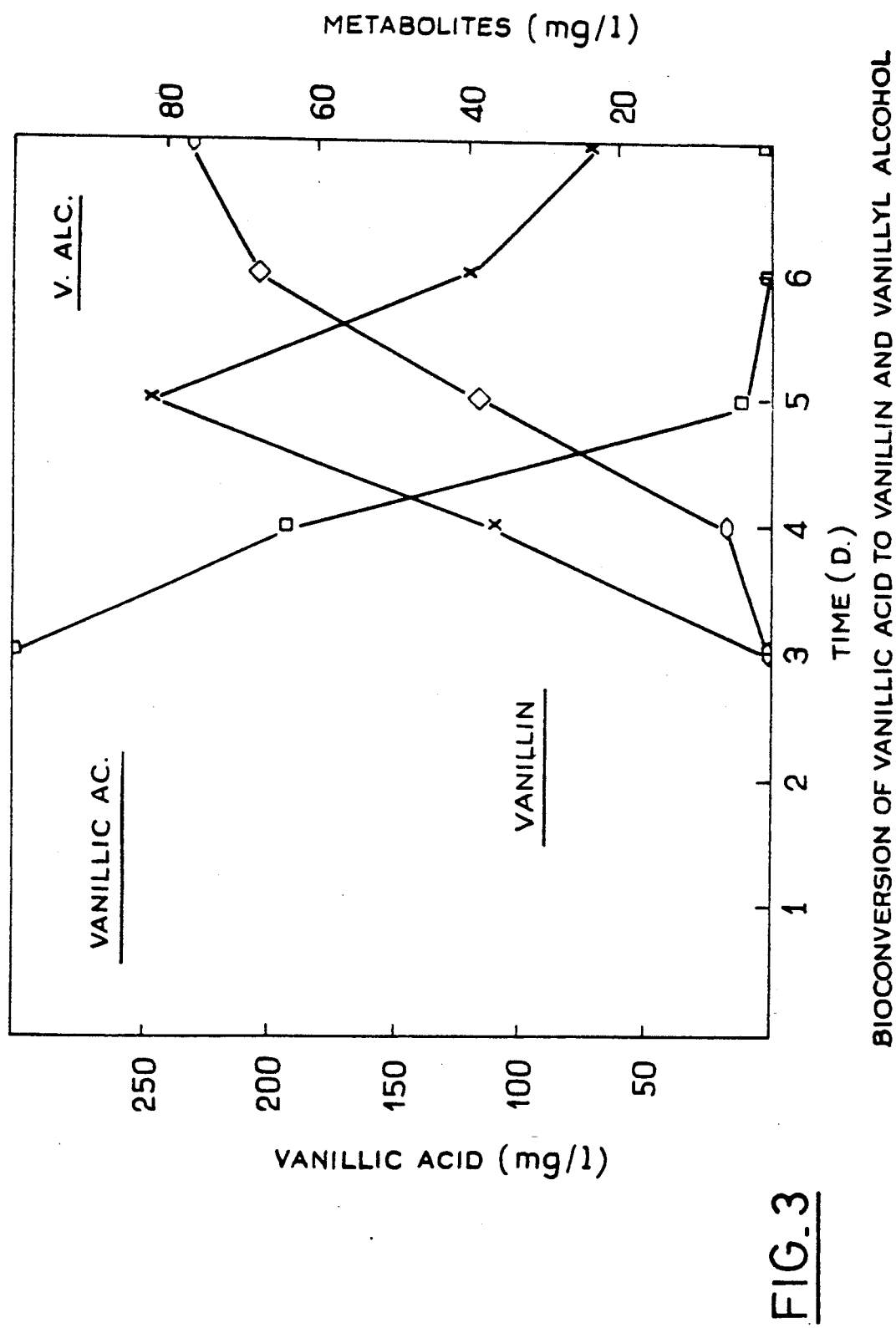
FIG. 3 shows the bioconversion of vanillic acid to vanillin and vanillyl alcohol.

| PRECURSOR ADDED ON DAY THREE OF CULTURE (see FIG. 3) | | | |
|---|---|---|---|
| Age of the culture (in d) | Vanillic acid precursor (in mg/l) | Vanillin (in mg/l) | Vanillyl Alcohol (in mg/l) |
| 3 | 300 | | |
| 4 | 191 | 35.7 | 5.1 |
| 5 | 10.3 | 81.4 | 38.9 |
| 6 | 1.2 | 39.4 | 68.2 |
| 7 | 2.1 | 23.4 | 76.5 |

The conditions of bioconversion are the same as before; the concentrations of vanillic acid and vanillin are thus similar, the vanillin concentration is maximal when the precursor concentration has fallen to 0 mg/l. The results of assay of vanillyl alcohol suggest that the vanillin is converted to its alcohol. In effect, the appearance of the alcohol is retarded by approximately 24 h relative to that of vanillin, and its concentration increases considerably when the vanillin disappears from the culture medium. One of the means of optimization of the production would be to block this reduction, which leads to the formation of vanillyl alcohol to the detriment of vanillin. The maximum molar yield of conversion to vanillin is comparable to that above: 31%.

2) Bioconversion of Ferulic Acid

Figure 4:
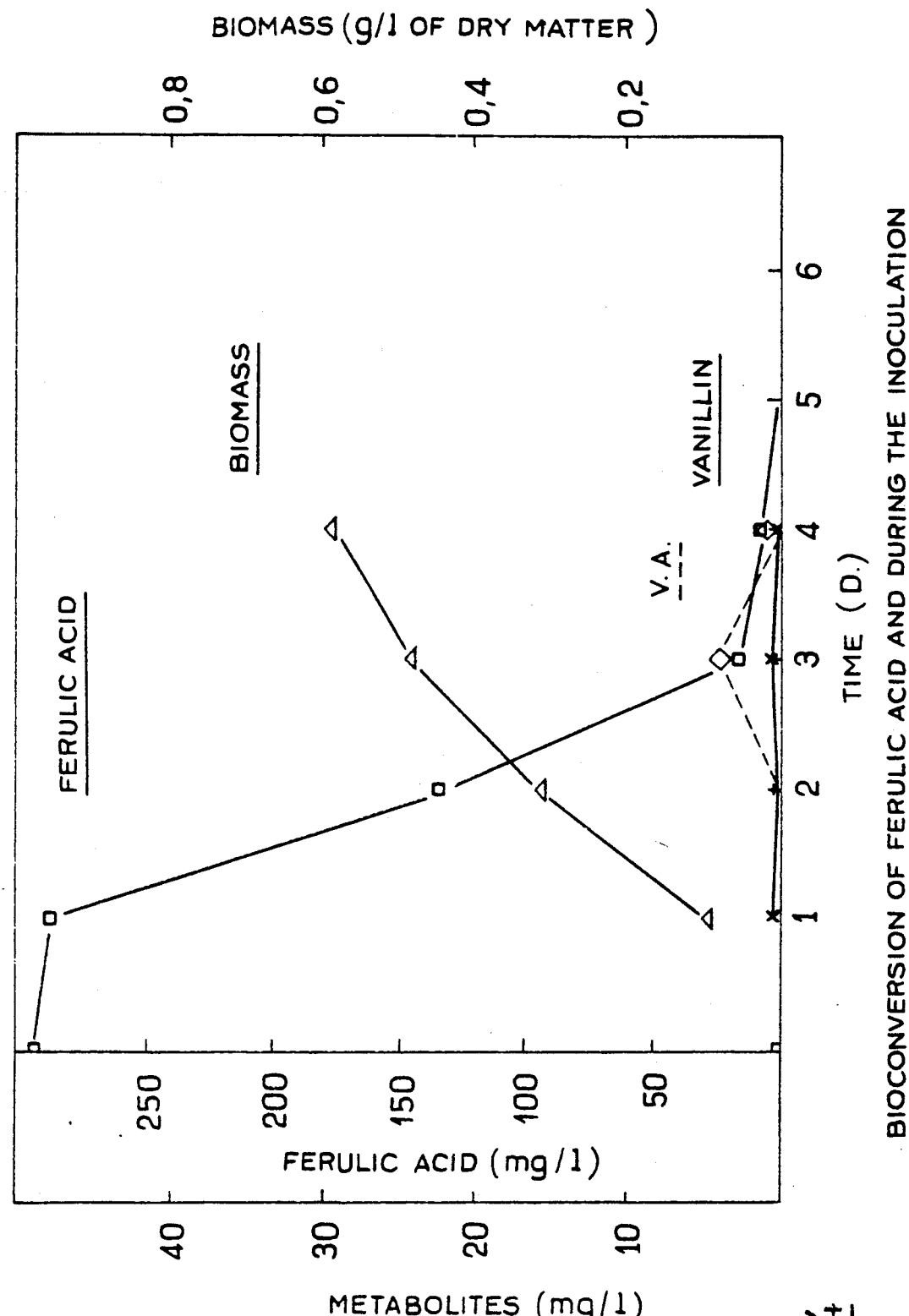
FIG. 4 shows the bioconversion of ferulic acid added with the inoculation.

| PRECURSOR ADDED DURING THE INOCULATION (see FIG. 4) | | | | |
|---|---|---|---|---|
| Age of the culture (in d) | Biomass in g of dry matter per l) | Ferulic acid precursor (in mg/l) | Vanillic acid (in mg/l) | Vanillin (in mg/l) |
| 0 | | 294 | | |
| 1 | 0.095 | 287 | | |
| 2 | 0.314 | 133.7 | | |
| 3 | 0.484 | 15.7 | 4.2 | 0.5 |
| 4 | 0.590 | 7.4 | 1.1 | 0.35 |

As in the case of vanillic acid added during the inoculation, the biomass increases considerably up to the last day of the study. Degradation of the ferulic acid is complete after 4–5 days. A synthesis of vanillic acid and of vanillin is observed, but the yields are rather low (maximum molar yield of conversion to vanillin: 0.2%).

Figure 5:
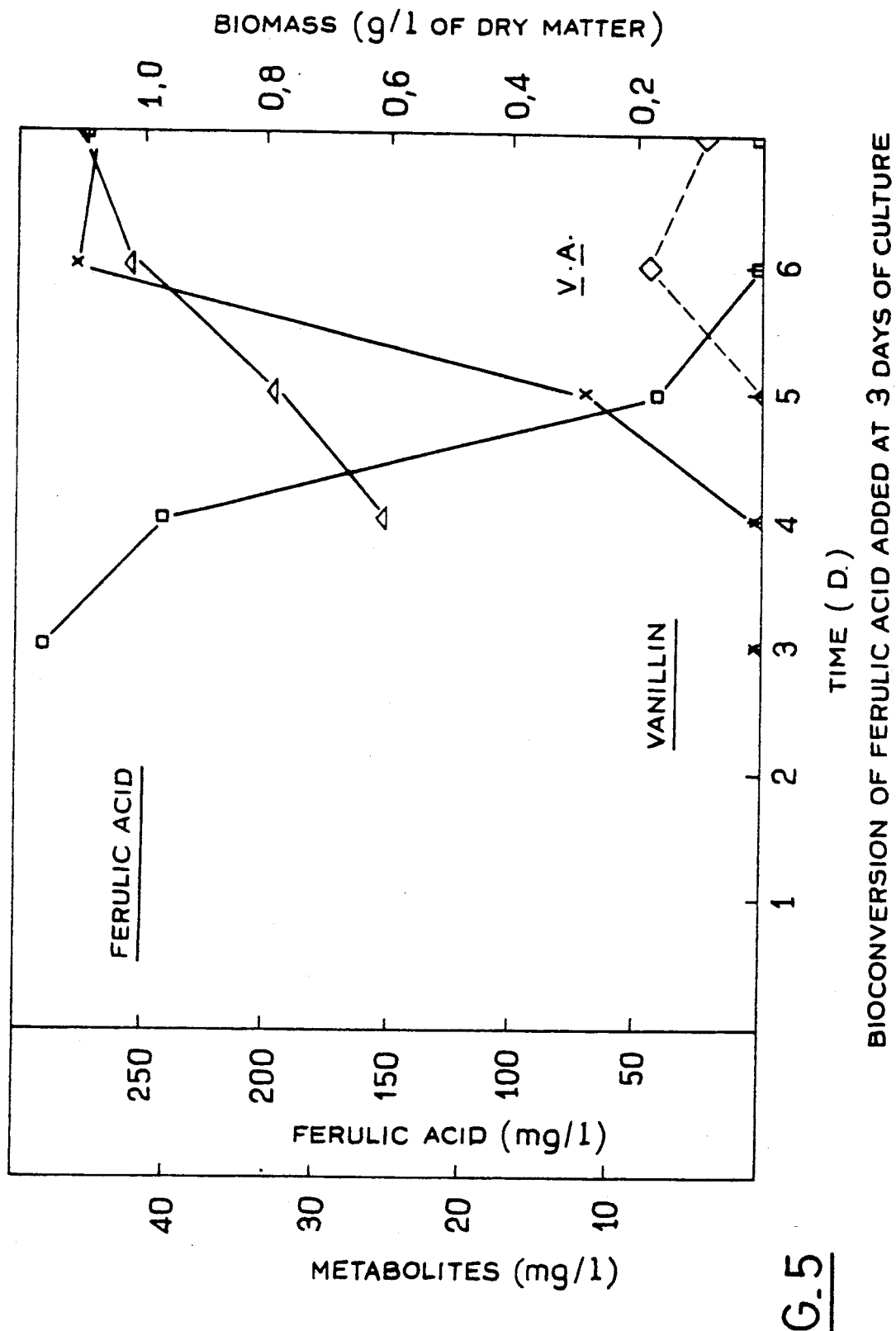
FIG. 5 shows the bioconversion of ferulic acid added at 3 days of culture.
- vanillic acid or ferulic acid, respectively
- vanillyl alcohol
- X vanillin
- biomass Vanillic Ac. or V.A. = vanillic acid
V. Alc. = vanillyl alcohol

| PRECURSOR ADDED ON DAY THREE OF CULTURE (see FIG. 5) | | | | |
|---|---|---|---|---|
| Age of the culture (in d) | Biomass in g of dry matter per l) | Ferulic acid precursor (in mg/l) | Vanillic acid (in mg/l) | Vanillin (in mg/l) |
| 3 | | 289 | | |
| 4 | 0.609 | 241 | | |
| 5 | 0.789 | 41.5 | | 11.5 |
| 6 | 1.023 | 0.9 | 7.7 | 46.2 |
| 7 | 1.099 | 0.85 | 4.1 | 45.4 |

In this case of supplementation at 3 days of culture, the ferulic acid disappears completely from the medium in 3 days. Simultaneous syntheses of vanillic acid and of vanillin are observed. As with vanillic acid, the quantity of vanillin is maximal when the precursor concentration becomes zero. The maximum molar yield of conversion to vanillin is: 20.5%.

We claim:
1. A process for the production of vanillin, said process comprising
providing a nutrient medium containing a benzenoid precursor of vanillin and assimilable sources of carbon and nitrogen and *Pycnoporus cinnabarinus* capable of producing vanillin from a benzenoid precursor of vanillin;
culturing said *Pycnoporus cinnabarinus* to produce vanillin; and
recovering said vanillin,
wherein said *Pycnoporus cinnabarinus* is selected from the group consisting of *Pycnoporus cinnabarinus* CNCM No. I-937 and *Pycnoporus cinnabarinus* CNCM No. I-938, and wherein said benzenoid precursor is selected from the group consisting of vanillic acid and ferulic acid.
2. The process of claim 1, wherein said benzenoid precursor is vanillic acid.
3. The process of claim 1, wherein said benzenoid precursor is ferulic acid.

4. The process of claim 1, wherein said precursor is added to the culture medium after three days of culture of *Pycnoporus cinnabarinus*.

5. The process of claim 1, wherein said *Pycnoporus cinnabarinus* is provided in a form selected from the group consisting of an inoculum consisting of mycelium fragments;

an inoculum consisting of spores;

a preculture of an inoculum consisting of mycelium fragments; and a preculture of an inoculum consisting of spores.

6. The process of claim 1, wherein said vanillin is recovered when said precursor is no longer detectable in the culture medium and before bioconversion of said vanillin to vanillyl alcohol.

7. The process of claim 1, wherein said precursor is introduced and said vanillin is recovered periodically.

8. The process of claim 1, wherein said precursor is introduced and said vanillin is recovered continuously.

9. The process of claim 4, wherein the amount of vanillin recovered is 40–90 mg/l.

10. The process of claim 4, wherein the amount of vanillin recovered is 70–90 mg/l.

* * * * *